United States Patent
Faulkner

(12) 
(10) Patent No.: US 6,579,542 B1
(45) Date of Patent: Jun. 17, 2003

(54) TREATING FELINE-SPECIFIC DISORDERS BY ORALLY ADMINISTERING *HYDRASTIS CANADENSIS*

(75) Inventor: Cecil Faulkner, 670 Water St. #1E, New York, NY (US) 10002

(73) Assignee: Cecil Faulkner, New York, NY (US)

( * ) Notice: Subject to any disclaimer, the term of this patent is extended or adjusted under 35 U.S.C. 154(b) by 0 days.

(21) Appl. No.: 09/517,344

(22) Filed: Mar. 2, 2000

(51) Int. Cl.$^7$ ................... A61K 35/78; A01N 65/00
(52) U.S. Cl. ....................... 424/726; 424/725
(58) Field of Search ............... 424/74, 76.9, 725, 424/726, 773, 93.7

(56) References Cited

U.S. PATENT DOCUMENTS

| | | | | |
|---|---|---|---|---|
| 4,599,228 A | * | 7/1986 | Ladanyi | 424/52 |
| 4,761,417 A | * | 8/1988 | Maroko | 514/284 |
| 5,634,431 A | * | 6/1997 | Reddy et al. | 119/173 |
| 5,955,086 A | * | 9/1999 | DeLuca et al. | 424/195.1 |
| 6,248,591 B1 | * | 6/2001 | Ali | 436/63 |
| 6,262,105 B1 | * | 7/2001 | Johnstone | 514/430 |

* cited by examiner

*Primary Examiner*—David M. Naff
*Assistant Examiner*—Deborah K. Wave

(57) ABSTRACT

*Hydrastis canadensis* is used for treating feline-specific disorders, such as, feline-specific fungi, feline specific-coat degradations, and feline-specific strong feces odors. At least one vitamin can also be added to the *hydrastis canadensis*. The *hydrastis canadensis* is taken orally by the feline either in tablet, powder, or liquid form.

12 Claims, No Drawings

TREATING FELINE-SPECIFIC DISORDERS BY ORALLY ADMINISTERING *HYDRASTIS CANADENSIS*

BACKGROUND OF THE INVENTION

1. Field of the Invention

The present invention relates to a formula. More particularly, the present invention relates to a multi-purpose formula for treating feline-specific disorders.

2. Description of the Prior Art

Felines suffer from disorders specific thereto, such as, for example, feline-specific fungi, feline specific-coat degradations, and feline-specific strong feces odors.

Numerous innovations for formulas have been provided in the prior art that will be described. Even though these innovations may be suitable for the specific individual purposes to which they address, however, they differ from the present invention in that the do not teach an oral treatment for feline-specific disorders, such as, for example, feline-specific fungi, feline specific-coat degradations, and feline-specific strong feces odors.

FOR EXAMPLE, U.S. Pat. No. 4,495,208 to Friedman et al. teaches a palatable, high-moisture pet food which is reliably stable against microbial attack without need to resort to pasteurization. This objective has long been sought by the art and is now met by the pet food provided by the invention which is a nutritionally-balanced pet food comprising protein, fat, carbohydrates, vitamins and minerals, has a moisture content within the range of from 50 to 80%, exhibits a water activity of at least 0.90, and further comprises on a total weight basis from 4% to 15% fructose; from 0.3% to 3.0% of an edible organic acid and sufficient inorganic acid to maintain the pH of the product within the range of from 3.5 to 5.8; and an antimycotic in an amount which is effective to prevent mold growth wherein the preservation system is bactericidal. According to a preferred embodiment the binders comprises carrageenan and the organic acid is selected from the group consisting of haptenic, octanoic, nonanoic and combination of these.

ANOTHER EXAMPLE, U.S. Pat. No. 5,021,424 to Lawton-Wall teaches an internally administered pharmaceutical preparation for treatment and prevention of flea infestations in animals, especially dogs and cats, and the associated allergic reaction, hair loss and irritation which accompany flea infestation. The active ingredients include Vitamin C, Vitamin B-1 and Biotin in a pharmaceutically acceptable carrier. The pharmaceutical preparation is preferably administered orally, once a day to the animal.

STILL ANOTHER EXAMPLE, U.S. Pat. No. 5,217,734 to Tanaka teaches PET bird feed additives in the form of fine granules obtained by mixing 100 parts by weight of a Dunaliella alga powder with 15 to 50 parts by weight of cyclodextrin under stirring and to 100 parts by weight of the mixed adsorbate thus obtained adding an antioxidant and a binder; a PET bird feed obtained by blending 5 to 15 parts by weight of the granules thus obtained with a common PET bird feed; and processes for producing them. In this PET bird feed additive, the Dunaliella alga powder is in the form of a mixed adsorbate together with cyclodextrin and thus .beta.-carotene contained in the Dunaliella alga can be stably sustained and effectively utilized. Further, the offensive odor characteristic to the algae can be removed. Furthermore, this PET bird feed additive, which is in the form of fine granules, can be easily blended with a common PET bird feed.

YET ANOTHER EXAMPLE, U.S. Pat. No. 5,776,903 to Dive et al. teaches peptide derivatives usable as zinc endopeptidase 24–15 inhibitors. These peptide derivatives have the following amino acid sequence: -Phe.psi.($PO_2$ $CH_2$)-.sub.(L,D) Xaa'-Yaa'-Zaa'- in which psi.($PO_2$ $CH_2$) indicates that the peptide bond (CONH) has been replaced by the phosphine bond ($PO_2$ $CH_2$), Xaa' and Zaa', which can be the same or different, in each case represent a natural amino acid or an amino pseudo-acid and Yaa' represents Arg or Lys. As examples of such derivatives, reference can be made to those of formula: Z-.sub.(L,D) Phe.psi.($PO_2$ $CH_2$)-.sub.(L,D)-Gly-Arg-MetOH Z-.sub. (L,D) Phe.psi.($PO_2$ $CH_2$)-sub.(L,D)-Ala-Arg-MetOH Z-.sub.(L,D) Phe.psi.($PO_2$ $CH_2$)-.sub.(L,D)-Ala-Arg-PheOH with Z representing the benzyloxycarbonyl group.

STILL YET ANOTHER EXAMPLE, U.S. Pat. No. 5,792,501 to Lepine teaches an artificially produced feline milk substitute composition. The composition comprises casein, whey, and as expressed on a dry matter basis, from about 30 to about 50 percent protein, from about 25 to about 50 percent fat, and from about 10 to about 25 percent lactose. The casein and whey in the composition have a ratio of about 1:1.

It is apparent that numerous innovations for formulas have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a multi-purpose formula for treating feline-specific disorders that avoids the disadvantages of the prior art.

ANOTHER OBJECT of the present invention is to provide a multi-purpose formula for treating feline-specific disorders that is simple and inexpensive to manufacture.

STILL ANOTHER OBJECT of the present invention is to provide a multi-purpose formula for treating feline-specific disorders that is simple to use.

BRIEFLY STATED, *hydrastis canadensis* is a highly regarded herb for humans, but its properties have never been recognized for treating feline-specific disorders, such as, for example, feline-specific fungi, feline specific-coat degradations, and feline-specific strong feces odors. At least one vitamin can also be added to the hydrastis canadensis. The *hydrastis canadensis* is taken orally by the feline either in tablet, powder, or liquid form.

The novel features which are considered characteristic of the present invention are set forth in the appended claims. The invention itself, however, both as to its composition and its method of use, together with additional objects and advantages thereof, will be best understood from the following description of the specific embodiments when read and understood.

DETAILED DESCRIPTION OF THE PREFERRED EMBODIMENT

*Hydrastis canadensis*, commonly called yellow paint root, orange root, yellow puccoon, ground raspberry, eye root, yellow Indian plant, tumeric root, Ohio curcuma, eye balm, yellow eye, and jaundice root, has the medicinal properties of a laxative, a tonic alterative, a detergent, an opthalmicum, an antiperiodic, an aperient, a diuretic, an antiseptic, and a deobstruent.

*Hydrastis canadensis* is one of the most wonderful remedies in the entire herb kingdom. When one considers all that can be accomplished by its use and what it actually will do, it seems like a real cure-all. It is especially valuable in all diseased states of the digestive system. It is a wonderful remedy for all stomach disorders and acute inflammations.

The wild plant of *hydrastis canadensis*, is nearly extinct in North america, but is being cultivated.

*Hydrastis canadensis* is one of the best substitutes for quinine, and is a most excellent remedy for colds, la grippe, and all kinds of stomach and liver troubles. It exerts a special influence on all the mucus membranes and tissues with which it comes in contact. For open sores, inflammations, eczema, ringworm, erysipelas, or any skin disease, *hydrastis canadensis* excels.

The tea of *hydrastis canadensis* is made by steeping one teaspoonful in a pint of boiling water for twenty minutes. The tea is used as a wash. Then after the area is thoroughly cleaned, the powered root is sprinkled on and the area is covered. The use of hydrogen peroxide for cleaning the area is also beneficial.

Taken in small, but frequent doses, *hydrastis canadensis* will allay nausea during pregnancy. Steep a teaspoon in a pint of boiling water for twenty minutes, stir well, let settle, and pour off the liquid. Take six tablespoonfuls a day. It equalizes the circulation.

When *hydrastis canadensis* is combined with skullcap and red pepper (cayenne), the heart will be greatly relieved and strengthened.

*Hydrastis canadensis* has no superior when combined with myrrh, one part *hydrastis canadensis* to one-fourth part myrrh, for an ulcerated stomach or duodenum or dyspepsia, and is especially good for enlarged tonsils and sores in the mouth. Smoker's sores, caused by holding a pipe in the mouth, will heal after just a few applications of the powder to the sore.

*Hydrastis canadensis* is an excellent remedy for diphtheria, tonsillitis, and other serious throat troubles, and has a good effect when combined with a little myrrh and cayenne. Excellent for chronic catarrh of the intestines and all catarrhal conditions will improve the appetite and aid digestion.

Combined with skullcap and hops, *hydrastis canadensis* is a very fine tonic for spinal nerves and is very good in spinal meningitis. Very useful in all skin eruptions, scarlet fever, and smallpox.

To cure pyorrhea or sore gums, put a little of the tea of *hydrastis canadensis* in a cup, dip a toothbrush in it, and thoroughly brush the teeth and gums. The results will be most satisfactory.

In any nose trouble, pour some tea of *hydrastis canadensis* in the hollow of the hand and sniff it up the nose.

*Hydrastis canadensis* is very useful in typhoid fever, gonorrhea, leukorrhea, and syphilis.

For bladder troubles, *hydrastis canadensis* should be introduced into the bladder through a catheter immediately after the bladder has been emptied and retained as long as possible, repeating two or three times a day.

*Hydrastis canadensis* combined with alum root, taken internally, is an excellent remedy for bowel and bladder troubles. Use two parts of *hydrastis canadensis* and one part of wild alum. This is a good laxative. Good for piles, hemorrhoids, and prostate troubles.

When *hydrastis canadensis* is combined with equal parts of red clover blossoms, yellow dock, and dandelion, it has a wonderful effect on the gallbladder, liver, pancreas, spleen, and kidneys.

When *hydrastis canadensis* is combined with peach leaves, queen of the meadow, cleavers, and corn silk, it is a reliable aid for Bright's disease and diabetes.

*Hydrastis canadensis* is excellent for the eyes. Steep one small teaspoonful of *hydrastis canadensis* and one of boric acid in a pint of boiling water, stir thoroughly, let cool, and pour liquid off. Put a tablespoonful of this liquid in a half cup of water. Bath the eyes with this, using an eye cup or drop it in with an eye dropper.

*Hydrastis canadensis* may be taken in different ways, and in all cases previously given where it is suggested to combine it with others, it may be used alone.

Take one-fourth teaspoonful of *hydrastis canadensis* dissolved in a glass of hot water immediately upon rising, and one hour before the noon and evening meals. Or you may steep a teaspoonful in a pint of boiling water, stir thoroughly, let cool, pour the liquid off and take a tablespoonful four to six times a day. Children should take less of all doses according to age.

Chronic catarrh (inflammation with a discharge) of the intestines, even to the extent of ulceration, is greatly benefited by *hydrastis canadensis*.

*Hydrastis canadensis* is effective in treating hemorrhage from the rectum and will heal ulcerations of the mucous lining in this area.

*Hydrastis canadensis* is a remedy for chronic and intermittent malaria and enlarged spleen caused by malaria.

*Hydrastis canadensis* kills and neutralizes many poisons.

*Hydrastis canadensis* is applicable in all catarrhal conditions, whether of the throat, nasal passages, bronchial tubes, intestines, stomach, bladder, or wherever there is a lining of mucus membrane.

As can be seen from the discussion supra, *hydrastis canadensis* is a highly regarded herb for humans, but its properties have never been recognized for treating feline-specific disorders, such as feline-specific fungi, feline specific-coat degradations, and feline-specific strong feces odors. At least one vitamin can also be added to the hydrastis canadensis. The *hydrastis canadensis* is taken orally by the feline either in tablet, powder, or liquid form.

While the invention has been illustrated and described as embodied in a multi-purpose formula for feline-specific disorders, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A method for treating feline-specific fungi, comprising the step of orally administering to a feline, a composition comprising *Hydrastis canadensis* and at least one vitamin.

2. The method as defined in claim 1, wherein said composition is in tablet form.

3. The method as defined in claim 1, wherein said composition is in powdered form.

4. The method as defined in claim 1, wherein said composition is in liquid form.

5. A method for impairing feline-specific coat degradation, comprising the step of orally administering to a feline a composition comprising *Hydrastis canadensis* and at least one vitamin.

6. The method as defined in claim 5, wherein said composition is in tablet form.

7. The method as defined in claim 5, wherein said composition is in powdered form.

8. The method as defined in claim 5, wherein said composition is in liquid form.

9. A method for eliminating feline-specific strong feces odors, comprising the step of orally administering to a feline a composition comprising *Hydrastis canadensis* and at least one vitamin.

10. The method as defined in claim 9, wherein said composition is in tablet form.

11. The method as defined in claim 9, wherein said composition is in powdered form.

12. The method as defined in claim 9, wherein said composition is in liquid form.

\* \* \* \* \*